United States Patent [19]

Cantello et al.

[11] Patent Number: 4,622,342

[45] Date of Patent: Nov. 11, 1986

[54] SECONDARY AMINES

[75] Inventors: Barrie C. C. Cantello, Redhill; Richard M. Hindley, Reigate, both of England

[73] Assignee: Beecham Group P.L.C., England

[21] Appl. No.: 667,548

[22] Filed: Nov. 2, 1984

Related U.S. Application Data

[63] Continuation of Ser. No. 396,719, Jul. 9, 1982, abandoned.

[30] Foreign Application Priority Data

Jul. 11, 1981 [GB] United Kingdom ............... 8121444
Mar. 10, 1982 [GB] United Kingdom ............... 8207005

[51] Int. Cl.[4] .................. C07C 91/06; A61K 31/13
[52] U.S. Cl. .................................... 514/653; 564/360; 564/363
[58] Field of Search ............... 424/330; 564/360, 363; 514/653

[56] References Cited

U.S. PATENT DOCUMENTS

| | | | |
|---|---|---|---|
| 3,954,871 | 5/1976 | Buu-Hoi et al. | 564/363 |
| 4,011,319 | 3/1977 | Kaiser et al. | 424/244 |
| 4,276,304 | 6/1981 | Ikeyoki et al. | 424/330 |
| 4,324,800 | 4/1982 | Umino et al. | 564/363 |
| 4,374,149 | 2/1983 | Philion | 564/363 |
| 4,382,958 | 5/1983 | Duckworth | 514/653 |
| 4,396,627 | 8/1983 | Ainsworth et al. | 514/653 |

FOREIGN PATENT DOCUMENTS

| | | | |
|---|---|---|---|
| 843422 | 4/1976 | Belgium | 564/360 |
| 208533 | 11/1982 | German Democratic Rep. | 514/653 |
| 1574208 | 9/1980 | United Kingdom | 564/363 |

Primary Examiner—James H. Reamer
Attorney, Agent, or Firm—Jacobs & Jacobs

[57] ABSTRACT

Compounds of formula (II):

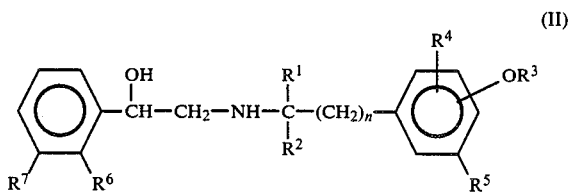

or salt thereof; wherein
$R^1$ is hydrogen or methyl,
$R^2$ is hydrogen or methyl,
$R^3$ is hydrogen, $C_{1-12}$ straight or branched alkyl, $C_{3-10}$ cycloalkyl, phenyl($C_{1-4}$)-alkyl or benzyl optionally substituted by $C_{1-4}$ alkyl, $C_{1-4}$ alkoxy or halogen;
$R^4$ is hydrogen, halogen, hydroxy, $C_{1-4}$ alkyl or $C_{1-4}$ alkoxy,
$R^5$ is hydrogen or fluorine,
$R^6$ is hydrogen or fluorine,
$R^7$ is halogen; and
n is 1 or 2, have anti-obesity and/or anti-hyperglycaemic activity.

21 Claims, No Drawings

SECONDARY AMINES

This is a continuation of Ser. No. 396,719 filed July 9, 1982, now abandoned.

The present invention relates to derivatives of ethanolamine which have anti-hyperglycaemic activity, to processes for their preparation and to their use in medicine. Some of these compounds also possess anti-inflammatory, and/or platelet-aggregation inhibiting and/or anti-obesity activity. These activities are coupled with low cardiac stimulation activity for certain of the derivatives.

Belgian Patent Specification No. 843422 discloses compounds of the formula (I):

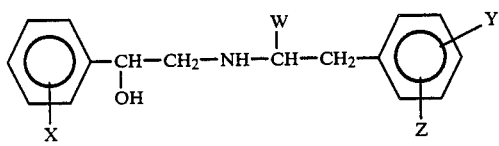

in which
  W is hydrogen or methyl,
  Y is hydrogen, methoxy or ethoxy,
  Z is methoxy or ethoxy, and
  X is hydrogen, chlorine, bromine, fluorine or methyl.

These compounds are disclosed as intermediates in the preparation of other compounds for treating Parkinson's disease. The intermediates themselves are not disclosed as having pharmaceutical activity in their own right.

U.K. Patent Specification No. 1,574,208 also discloses compounds of formula (I) wherein W is hydrogen, Y is hydrogen or methoxy, Z is methoxy, and X is hydrogen, chlorine, bromine, fluorine, methyl, trifluoromethyl or methoxy. These compounds are also disclosed as intermediates in the preparation of other compounds for treating Parkinson's disease, and are not disclosed as having pharmaceutical activity.

We have now discovered a group of compounds, some of which fall within the scope of formula (I) but, with a single exception, none of which are specifically disclosed in Belgian Pat. No. 843422 or U.K. Pat. No. 1,574,208, which have anti-hyperglycaemic and anti-obesity activity. These activities could not have been predicted from the aforementioned patent specifications.

According to the present invention there is provided a compound of formula (II):

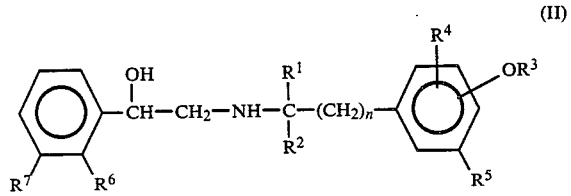

or a salt thereof; wherein
  $R^1$ is hydrogen or methyl,
  $R^2$ is hydrogen or methyl,
  $R^3$ is hydrogen, $C_{1-12}$ straight or branched alkyl, $C_{3-10}$ cycloalkyl, phenyl $(C_{1-4})$alkyl or benzyl optionally substituted by $C_{1-4}$ alkyl, $C_{1-4}$ alkoxy or halogen;
  $R^4$ is hydrogen, halogen, hydroxy, $C_{1-4}$ alkyl or $C_{1-4}$ alkoxy,
  $R^5$ is hydrogen or fluorine,
  $R^6$ is hydrogen or fluorine,
  $R^7$ is halogen; and
  n is 1 or 2,
provided that when $R^1$, $R^2$ and $R^6$ are each hydrogen, $-OR^3$ is para methoxy, $R^4$ is methoxy, $R^5$ is hydrogen, $R^7$ is chloro and n is 1, then $R^4$ is ortho to the group $-(CH_2)_n-$.

Preferably n is 1.
Preferably $R^1$ is hydrogen and $R^2$ is methyl.
Preferably $R^4$ is hydrogen or fluorine.
Preferably $R^7$ is chlorine.

Pharmaceutically acceptable salts of compounds of formula (II) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.

In the case where $R^3$ is hydrogen, the salts may include alkali metal and alkaline earth metal salts.

The salts of compounds of formula (II) need not be pharmaceutically acceptable as they are also useful in the preparation of other compounds of formula (II) and in the separation of stereoisomers of compounds of formula (II) when the salt ion is also optically active.

The salts of compounds of formula (II) may be produced by treating the compound of formula (II) with the appropriate acid.

Compounds of formula (II) have at least one asymmetric carbon atom, i.e. the one bearing the hydroxyl and m-halophenyl group, and, when $R^1$ and $R^2$ are different, the carbon atom bearing $R^1$ and $R^2$ is also asymmetric. The compounds may, therefore, exist in at least two and often four stereoisomeric forms. The present invention encompasses all stereoisomers of the compounds of formula (II) whether free from other stereoisomers or admixed with other stereoisomers in any proportion and thus includes, for instance, racemic mixtures of enantiomers.

Preferably, the carbon atom bearing the hydroxyl and m-halophenyl group has the R-absolute configuration.

The most potent compounds of formula (II) are those wherein $R^1$ and $R^2$ are different and both asymmetric carbon atoms are in the R-absolute configuration.

The absolute configuration of any compound of formula (II) may be determined by conventional X-ray crystallographic techniques.

It is believed that, in the $^{13}C$ nmr of compounds of formula (II) wherein one of $R^1$ and $R^2$ is hydrogen and the other is methyl, the diastereoisomer having the greater anti-obesity and anti-hyperglycaemic activity is that for which the signal of the methyl group carbon atom appears at higher field (the lower numerical value when expressed in ppm) in $d_6$DMSO solution. The paired resonances often appear at approximately 20 ppm (less active) and slightly below 20 ppm (more active) down field from tetramethylsilane. Other paired resonances can occur for the carbon atoms attached directly to the nitrogen atom and the carbon which carries the hydroxyl and phenyl groups. Again the paired resonances of the more active diastereoisomer of the investigated compounds appear at the higher field position.

The present invention also provides a process for producing a compound of formula (II) or a salt thereof, which process comprises reducing an oxo-group and/or a double bond and/or cleaving a benzyl group in a compound of formula (III):

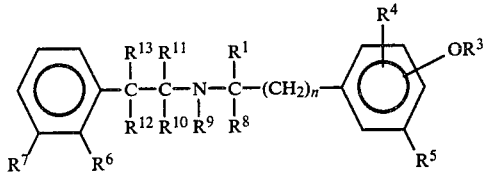
(III)

wherein
$R^1$, $R^3$, $R^4$, $R^5$, $R^6$, $R^7$ and n are as defined in relation to formula (II), $R^8$ is a group $R^2$ as defined in relation to formula (II) or together with $R^8$ forms a bond, $R^9$ is hydrogen, benzyl or together with $R^8$ or $R^{10}$ forms a bond, $R^{10}$ is hydrogen or together with $R^{11}$ forms an oxo-group or together with $R^9$ forms a bond, $R^{11}$ is hydrogen or together with $R^{10}$ forms an oxo-group, $R^{12}$ is hydroxyl or together with $R^{13}$ forms an oxo-group, $R^{13}$ is hydrogen or together with $R^{12}$ forms an oxo-group;

provided that there is no more than one oxo-group represented by any of $R^{10}$ to $R^{13}$, and optionally thereafter forming a salt of the compound of formula (II) so formed.

The aforementioned reduction may be effected by conventional chemical or catalytic methods, such as chemical reduction using lithium aluminium hydride, borane methyl sulphide complex, sodium cyanoborohydride or sodium borohydride or by catalytic hydrogenation using catalysts such as palladium on charcoal, or platinum, for instance, as platinum oxide.

Reduction by sodium borohydride is conveniently effected in a lower alkanolic solvent such as methanol or ethanol. The reaction is generally carried out between 0°–20° C.

Reduction by lithium aluminium hydride is conveniently effected in a dry, ether solvent such as diethyl ether or tetrahydrofuran at ambient or elevated temperature.

Catalytic reduction is conveniently effected in a conventional hydrogenation solvent such as a lower alkanol, for instance ethanol. The hydrogenation is generally carried out under hydrogen gas at about 1 atmosphere pressure and at ambient or elevated temperature.

Preferred aspects of the process for producing compounds of formula (II) comprise:
(a) reducing a compound of formula (IIIA):

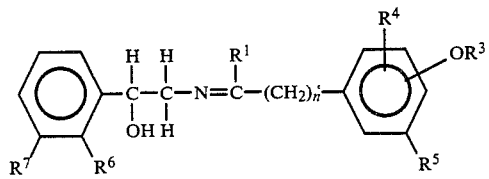
(IIIA)

or (b) reducing a compound of formula (IIIB):

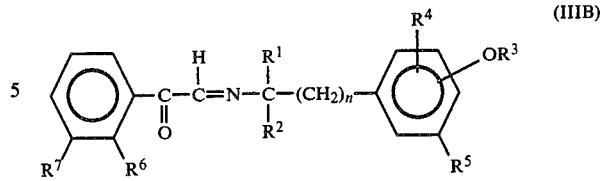
(IIIB)

or (c) reducing a compound of formula (IIIC):

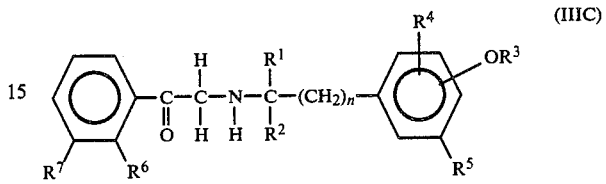
(IIIC)

or the N-benzyl derivative thereof; or (d) reducing a compound of formula (IIID):

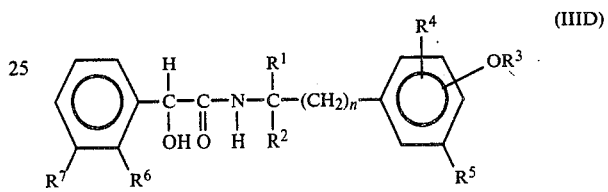
(IIID)

wherein $R^1$, $R^2$, $R^3$, $R^4$, $R^5$, $R^6$, $R^7$ and n are as defined in relation to formula (II).

A particularly preferred process for producing a compound of formula (II) comprises the reduction of a compound of formula (IIIA), especially using sodium borohydride in methanol at ambient temperature.

A particularly preferred process for producing a compound of formula (II) in which $R^3$ is hydrogen, comprises the reduction of a compound of formula (II) in which $R^3$ is benzyl. This reduction is conveniently carried out by catalytic hydrogenation in ethanol, using palladium on charcoal. A compound of formula (II) in which $R^3$ is hydrogen may also be produced by carrying out an ether cleavage with, for example, hydrobromic acid on a compound of formula (II) in which $R^3$ is alkyl.

The present invention also provides a further process for producing a compound of formula (II) or a salt thereof, which process comprises reacting a compound of formula (IV):

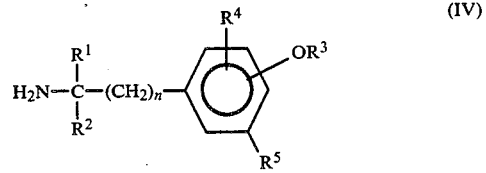
(IV)

with a compound of formula (V):

(V)

wherein

R$^1$, R$^2$, R$^3$, R$^4$, R$^5$, R$^6$, R$^7$ and n are as defined in relation to formula (II); and Y$^1$ is a group capable of reacting with the amine of formula (IV) thus forming a compound of formula (II), and optionally thereafter forming a salt of the compound of formula (II) so formed.

Typical examples of compounds of formula (V) include compounds of formulae (VA) and (VB):

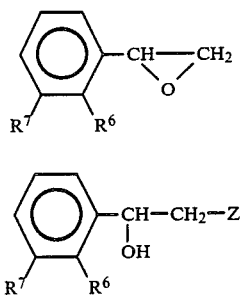

(VA)

(VB)

wherein

R$^6$ and R$^7$ are as defined in relation to formula (II), and

Z is a leaving group, preferably halogen, tosyloxy or mesyloxy.

The reaction of a compound of formula (VA) with a compound of formula (IV) is conveniently effected in a solvent such as a lower alkanol, preferably ethanol.

The present invention provides a further process for producing compounds of formula (II), which process comprises reacting a compound of formula (VI):

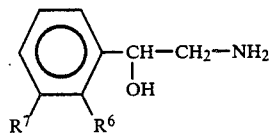

(VI)

with a compound of formula (VII):

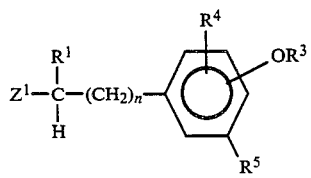

(VII)

wherein

R$^1$, R$^3$, R$^4$, R$^5$, R$^6$, R$^7$ and n are as defined in formula (II) and Z$^1$ is a leaving group, preferably halogen, tosyloxy or mesyloxy.

This reaction is conveniently effected in a solvent such as dimethylsulphoxide at an elevated temperature, preferably about 50° C. for about two or three days.

Compounds of formula (II) and salts thereof, produced by the above processes, may be recovered by conventional methods.

Compounds of formula (III) may themselves be produced by reacting a compound of formula (IV) as hereinbefore defined, with a compound of formula (VIII):

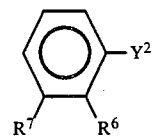

(VIII)

wherein Y$^2$ is a moiety which is capable of reacting with the amine of formula (IV) thus forming a compound of formula (III).

Typical examples of compounds of formula (VIII) are:

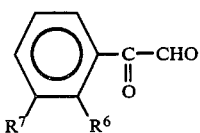

(VIIIA)

or its hydrate or hemi-acetal of a lower alkanol;

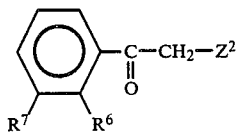

(VIIIB)

wherein Z$^2$ is halogen, preferably bromine; and

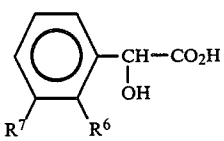

(VIIIC)

Conventional conditions suitable for use with the particular compound of formula (VIII) may be used for this reaction. Thus the reaction of a compound of formula (VIIIA) with a compound of formula (IV) is conveniently conducted at elevated temperature under conditions resulting in the removal of the water formed during the reaction. A particularly suitable method is to perform the reaction in a solvent, such as benzene, under reflux and azeotropically to remove the water using a Dean and Stark trap.

The reaction of a compound of formula (VIIIB) with a compound of formula (IV) is conveniently conducted in a polar organic solvent such as acetonitrile or butanone, at an elevated temperature, for instance under reflux.

The reaction of a compound of formula (VIIIC) with a compound of formula (IV) is conveniently conducted under standard peptide formation reaction conditions.

In one aspect of the above process for producing compounds of formula (III), the N-benzyl derivative of a compound of formula (IV) may be reacted with a compound of formula (VIIIB). In this case the N-benzyl derivative of formula (IIIC) is produced and this may be reduced to a compound of formula (II) using a catalytic hydrogenation reaction, especially using palladium on charcoal as catalyst.

A particularly preferred process for preparing compounds of formula (IIIA) comprises reacting a compound of formula (VI), as hereinbefore defined, with a compound of the formula (IX):

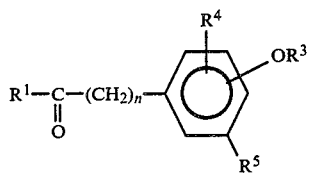

wherein $R^1$, $R^3$, $R^4$, $R^5$ and n are as defined in relation to formula (II).

The reaction of a compound of formula (VI) with a compound of formula (IX) is conveniently effected under conditions which result in the removal of water formed during the reaction. A particularly suitable method is to perform the reaction in a solvent, such as benzene or toluene, under reflux and azeotropically to remove the water using a Dean and Stark trap.

It is often convenient to prepare the compound of formula (III) and reduce it to the desired compound of formula (II) without isolation of the compound of formula (III).

Compounds of formula (II) having a single asymmetric carbon atom may, if desired, be separated into individual enantiomers by conventional means, for example by the use of an optically active acid as a resolving agent. Those compounds of formula (II) having two asymmetric carbon atoms may be separated into diastereoisomeric pairs of enantiomers by, for example, fractional crystallisation from a suitable solvent such as ethyl acetate. The pair of enantiomers thus obtained may be separated into individual stereoisomers by conventional means such as by the use of an optically active acid as a resolving agent.

Suitable optically active acids which may be used as resolving agents are described in "Topics of Stereochemistry", Vol. 6, Wiley Interscience, 1971, Allinger, N. L. and Eliel W. L. Eds.

Alternatively any enantiomer of a compound of formula (II) may be obtained by stereospecific synthesis using an optically pure starting material of known configuration.

By using single enantiomers of a compound of formula (IV) and a compound of formula (VIIIC), a stereospecific synthesis of a compound of formula (III) is achieved. This may then be reduced to a compound of formula (II) without altering the configuration of the two asymmetric carbon atoms. By using single enantiomers of a compound of formula (IV) and a compound of formula (VA) or (VB) a stereospecific synthesis of a compound of formula (II) is achieved directly. Thus, for example, a compound of formula (IV) with the R-absolute configuration and a compound of formula (VA) with the R-absolute configuration would afford a compound of formula (II) with the RR-absolute configuration.

A compound of formula (X):

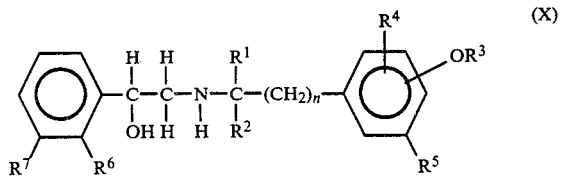

or a salt thereof; wherein
$R^1$ is hydrogen or methyl,
$R^2$ is hydrogen or methyl,
$R^3$ is hydrogen, $C_{1-12}$ straight or branched alkyl, $C_{3-10}$ cycloalkyl or phenyl $(C_{1-4})$alkyl or benzyl optionally substituted by $C_{1-4}$ alkyl, $C_{1-4}$ alkoxy or halogen;
$R^4$ is hydrogen, halogen, hydroxy, $C_{1-4}$ alkyl or $C_{1-4}$ alkoxy,
$R^5$ is hydrogen or fluorine,
$R^6$ is hydrogen or fluorine,
$R^7$ is halogen; and
n is 1 or 2, or a pharmaceutically acceptable salt thereof (hereinafter "the drug") may be administered as the pure drug; however, it is preferred that the drug be administered as a pharmaceutical composition also comprising a pharmaceutically acceptable carrier.

Accordingly, the present invention also provides a pharmaceutical composition comprising a compound of formula (X) or a pharmaceutically acceptable salt thereof with a pharmaceutically acceptable carrier therefor.

As used herein the terms "pharmaceutical composition" and "pharmaceutically acceptable" embrace compositions and ingredients for both human and veterinary use.

Usually the compositions of the present invention will be adapted for oral administration but administration by other routes, such as by injection, is also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, binder, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 500 mg of the drug, more usually 0.1 to 250 mg and favourably 0.1 to 100 mg.

The present invention further provides a method for treating hyperglycaemia in humans or animals which method comprises administering an effective, non-toxic amount of a compound of formula (X) or a pharmaceutically acceptable salt thereof to hyperglycaemic humans or animals.

The present invention also provides a method for treating obesity in humans or animals, which method comprises administering an effective non-toxic amount of a compound of formula (X) or a pharmaceutically acceptable salt thereof to obese humans or animals.

Conveniently, the drug may be administered as a pharmaceutical composition as hereinbefore defined, and this forms a particular aspect of the present invention.

In treating hyperglycaemic or obese humans the drug may be taken in doses, such as those described above, one to six times a day in a manner such that the total daily dose for a 70 kg adult will generally be about 0.1 to 1000 mg, and more usually about 1 to 500 mg.

In treating hyperglycaemic or obese animals, especially dogs, the drug may be administered by mouth, usually once or twice a day and at about 0.025 mg/kg to 10 mg/kg, for example 0.1 mg/kg to 2 mg/kg.

The present invention also provides a method for treating inflammation in humans, which comprises topically administering an effective, non-toxic, amount of a compound of formula (X) or a pharmaceutically acceptable salt thereof to humans suffering from inflammation.

The present invention also provides a method for inhibiting platelet aggregation in humans, which comprises administering an effective, non-toxic, amount of a compound of formula (X) or a pharmaceutically acceptable salt thereof.

The invention will now be illustrated with reference to the following Examples.

As used in the Examples, the term "diastereoisomer" refers to a racemic pair of enantiomers.

EXAMPLE 1

N-[2-(4-Benzyloxyphenyl)-1-methylethyl]-2-hydroxy-2-(3-chlorophenyl)ethanamine

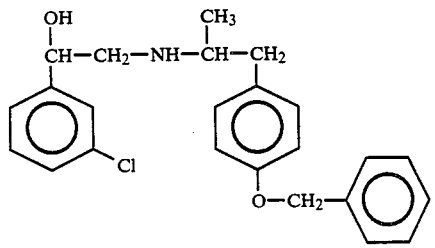

1-(4-Benzyloxyphenyl)propan-2-one (2.28 g) was added to a solution of 2-hydroxy-2-(3-chlorophenyl)ethanamine (1.75 g) in dry toluene (100 ml) and the solution was boiled under reflux for 90 minutes in an apparatus incorporating a water-trap. The solution was cooled and the solvent removed under reduced pressure. The residue, dissolved in methanol (100 ml), was cooled to less than 10° C. and treated portionwise with sodium borohydride (3.0 g) over 30 minutes, with stirring. The mixture was stirred for one hour at room temperature and the solvent removed under reduced pressure. The residue was dissolved in ethyl acetate, washed with water, dried (magnesium sulphate), filtered and evaporated to dryness to give a solid. Trituration of the solid with diethyl ether followed by addition of hexane and filtration gave N-[2-(4-benzyloxyphenyl)-1-methylethyl]-2-hydroxy-2-(3-chlorophenyl)ethanamine of analytical purity, mp 95°–99° C., as a 45:55 mixture of diastereoisomers.

$^1$Hnmr: $\tau$(CDCl$_3$): 8.95 (3H, d, J=6Hz), 6.8–7.6 (7H, m), 5.4 (1H, m), 5.0 (2H, s), 2.4–3.3 (13H, complex).

EXAMPLE 2

N-[2-(4-Hydroxyphenyl)-1-methylethyl]-2-hydroxy-2-(3-chlorophenyl)ethanamine

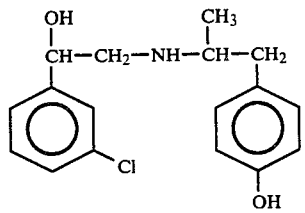

A mixture of 1-(4-hydroxyphenyl)propan-2-one (4.6 g) and 2-hydroxy-2-(3-chlorophenyl)ethanamine (5.2 g) in dry benzene (150 ml) was heated under reflux using a Dean and Stark head until the required amount of water had been collected. The solution was cooled, the solvent evaporated, the residue dissolved in methanol (20 ml), cooled in ice and treated portionwise with sodium borohyride (6.1 g) over 30 minutes. The mixture was stirred for 40 minutes, and the solvent removed under reduced pressure. Water was added to the residue and the mixture adjusted to pH 5 by addition of acetic acid followed by extraction with ethyl acetate. The extracts were washed with water, aqueous sodium bicarbonate and brine, dried (magnesium sulphate), filtered and evaporated to dryness. Chromatography of the residue on silica gel in 5% methanoldichloromethane gave N-[2-(4-hydroxyphenyl)-1-methylethyl]-2-hydroxy-2-(3-chlorophenyl)ethanamine mp 50°–5° C., of analytical purity as a 53:47 mixture of diastereoisomers.

$^1$Hnmr: $\tau$(DMSO$_6$): 9.1 (3H, d, J=6 Hz), 6.3–7.8 (8H, complex) collapsing to 7.05–7.8 (5H, complex) on D$_2$O exchange, 5.4 (1H, m), 3.30–3.5 (2H, d), 3.0–3.25 (2H, d), 2.5–2.9 (4H, m).

EXAMPLE 3

N-[2-(3-Fluoro-4-methoxyphenyl)-1-methylethyl]-2-hydroxy-2-(3-chlorophenyl)ethanamine

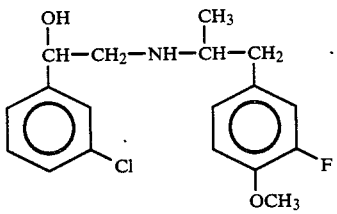

1-(3-Fluoro-4-methoxyphenyl)propan-2-one (2.73 g) and 2-hydroxy-2-(3-chlorophenyl)ethanamine (2.58 g) were condensed and subsequently reduced with sodium borohydride (2.0 g) by a procedure analogous to that described in Example 1, except dichloromethane was used instead of ethyl acetate in the work-up. Chromatography of the residue on silica gel in 5% methanol-dichloromethane gave N-[2-(3-fluoro-4-methoxyphenyl)-1-methylethyl]-2-hydroxy-2-(3-chlorophenyl)ethanamine, mp 93°–5° C. (diethyl ether) as a 55:45 mixture of diastereoisomers.

$^1$Hnmr $\tau$(CDCl$_3$): 8.90 (3H, d, J=6 Hz), 6.95–7.6 (7H, complex; 2H replaceable on D$_2$O exchange), 6.15 (3H, s), 5.4 (1H, m) 3.0–3.3 (3H, complex), 2.55–2.9 (4H, complex).

EXAMPLE 4

N-[2-(3-Fluoro-4-methoxyphenyl)-1-methylethyl]-2-hydroxy-2-(3-chlorophenyl)ethanamine hydrobromide-(RR,SS) diastereoisomer

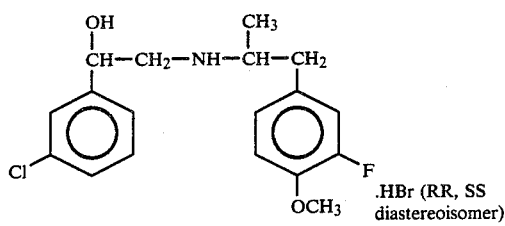

Hydrogen bromide was passed through a solution of N-[2-(3-fluoro-4-methoxyphenyl)-1-methylethyl]-2-hydroxy-2-(3-chlorophenyl)ethanamine (55:45 mixture of diastereoisomers) in diethyl ether until precipitation was complete. The solvent was removed under vacuum and the residual solid recrystallised from ethyl acetate-methanol to give N-[2-(3-fluoro-4-methoxyphenyl)-1-methylethyl]-2-hydroxy-2-(3-chlorophenyl)ethanamine hydrobromide-(RR,SS) diastereoisomer, mp 191°–5° C., of analytical purity and of 96% diastereoisomeric purity.

EXAMPLE 5

N-[2-(4-Methoxyphenyl)-1-methylethyl]-2-hydroxy-2-(3-chlorophenyl)ethanamine

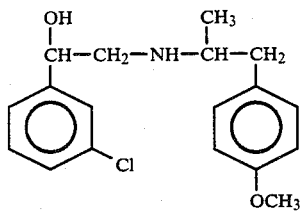

1-(4-Methoxyphenyl)propan-2-one (2.9 g) and 2-hydroxy-2-(3-chlorophenyl)ethanamine (3.03 g) were condensed and subsequently reduced with sodium borohydride (3.55 g) by an analogous procedure to that described in Example 1. The crude product was recrystallised from diethyl ether-hexane to give N-[2-(4-methoxyphenyl)-1-methylethyl]-2-hydroxy-2-(3-chlorophenyl)ethanamine, mp 80°–7° C., as a 45:55 mixture of diastereoisomers.

[1]Hnmr $\tau$(CDCl$_3$): 8.95 (3H, d), 6.95–7.65 (7H, 2H exchange with D$_2$O), 6.25 (3H, s), 5.45 (1H, m), 2.6–3.3 (8H, complex).

EXAMPLE 6

N-[2-(4-Methoxyphenyl)-1-methylethyl]-2-hydroxy-2-(3-chlorophenyl)ethanamine hydrobromide-(RR,SS) diastereoisomer

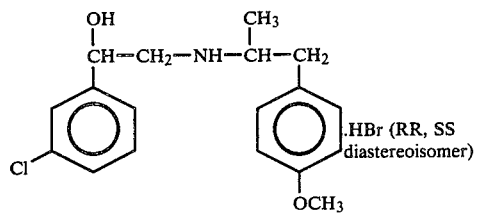

N-[2-(4-Methoxyphenyl)-1-methylethyl]-2-hydroxy-2-(3-chlorophenyl)ethanamine (1.1 g; 45:55 diastereoisomeric ratio) was dissolved in diethyl ether-methanol, cooled to 5° C. and hydrogen bromide gas passed through the solution and the solvent decanted from the precipitated oil. The oil was dissolved in ethyl acetate-diethyl ether and allowed to cool. Filtration gave N-[2-(4-methoxyphenyl)-1-methylethyl]-2-hydroxy-2-(3-chlorophenyl)ethanamine hydrobromide-(RR,SS) diastereoisomer, mp 172°–4° C., of 89% diastereoisomeric purity.

EXAMPLE 7

N-[2-(4-Methoxyphenyl)-1-methylethyl]-2-hydroxy-2-(3-fluorophenyl)ethanamine

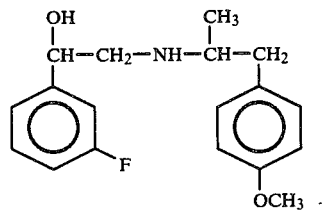

1-(4-Methoxyphenyl)propan-2-one (2.25 g) and 2-hydroxy-2-(3-fluorophenyl)ethanamine (2.13 g) were condensed and subsequently reduced with sodium borohydride (2.75 g) by an analogous procedure to that described in Example 1. The crude product was recrystallised from diethyl ether-hexane to give N-[2-(4-methoxyphenyl)-1-methylethyl]-2-hydroxy-2-(3-fluorophenyl)ethanamine, mp 85°–9° C., as a 37:63 mixture of diastereoisomers.

[1]Hnmr $\tau$(CDCl$_3$): 8.95 (3H, d), 6.9–7.7 (7H, complex, 2H exchange with D$_2$O), 6.2 (3H, s), 5.35 (1H, m), 2.5–3.25 (8H, complex).

EXAMPLE 8

N-[2-(4-Methoxyphenyl)-1-methylethyl]-2-hydroxy-2-(3-bromophenyl)ethanamine

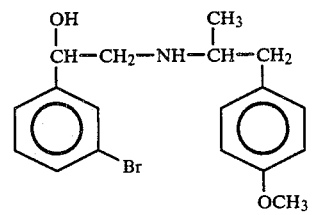

1-(4-Methoxyphenyl)propan-2-one (3.10 g) and 2-hydroxy-2-(3-bromophenyl)ethanamine (4.08 g) were condensed and subsequently reduced with sodium borohydride (3.8 g) by an analogous procedure to that described in Example 1. The crude product was recrystallised from diethyl ether-hexane to give N-[2-(4-methoxyphenyl)-1-methylethyl]-2-hydroxy-2-(3-bromophenyl)ethanamine, mp 79°–83° C., as a 47:53 mixture of diastereoisomers.

$^1$Hnmr $\tau$(CDCl$_3$): 8.9 (3H, d), 6.9–7.7 (7H, complex; 2H exchange with D$_2$O), 6.25 (3H, s), 5.4 (1H, m), 2.4–3.3 (8H, complex).

EXAMPLE 9

N-[2-(4-Methoxyphenyl)-1-methylethyl]-2-hydroxy-2-(3-chloro-2-fluorophenyl)ethanamine

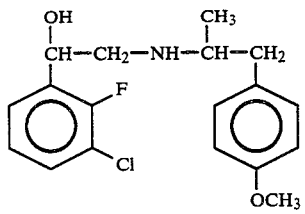

1-(4-Methoxyphenyl)propan-2-one (0.57 g) and 2-hydroxy-2-(3-chloro-2-fluorophenyl)ethanamine (0.65 g) were condensed and subsequently reduced with sodium borohydride (1.5 g) by an analogous procedure to that described in Example 1. Purification by column chromatography on silica gel using 2% methanol in dichloromethane gave an oil, trituration of which with hexane-petroleum ether, bp 40°–60° C., gave N-[2-(4-methoxyphenyl)-1-methylethyl]-2-hydroxy-2-(3-chloro-2-fluorophenyl)ethanamine, as a white solid, mp 95°–101° C., as a 33:67 mixture of diastereoisomers.

$^1$Hnmr $\tau$(DMSO-d$_6$+D$_2$O): 9.1 (3H, d), 7.0–7.7 (5H, complex), 6.3 (3H, s), 5.15 (1H, t), 2.4–3.3 (7H, complex).

EXAMPLE 10

N-[3-(4-Hydroxyphenyl)-1-methylpropyl]-2-hydroxy-2-(3-chlorophenyl)ethanamine

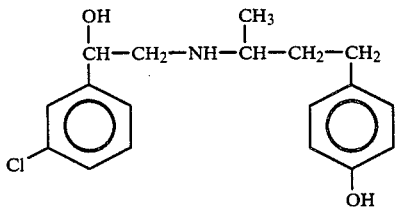

A mixture of 1-(4-hydroxyphenyl)butan-3-one (2.74 g) and 2-hydroxy-2-(3-chlorophenyl)ethanamine (2.86 g) in dry benzene (250 ml) was heated under reflux for two hours in an apparatus incorporating a water-trap. The solution was cooled and the solvent removed under reduced pressure. The residue, dissolved in methanol (100 ml), was cooled to less than 10° C. and treated portionwise with sodium borohydride (4.4 g) over 30 minutes, with stirring. The mixture was stirred for a further 90 minutes and the solvent removed under reduced prssure. Water was added to the residue and the pH adjusted to 5 by addition of acetic acid. The mixture was extracted with ethyl acetate and the extracts washed with aqueous sodium bicarbonate and brine, dried (magnesium sulphate) and evaporated to dryness. Chromatography of the residue on silica gel using 7% methanol in dichloromethane gave, after subsequent trituration with diethyl ether-hexane, N-[3-(4-hydroxyphenyl)-1-methylpropyl]-2-hydroxy-2-(3-chlorophenyl)ethanamine, mp 103°–110° C., as a 50:50 mixture of diastereoisomers.

$^1$Hnmr $\tau$(DMSO-d$_6$): 9.0 (3H, d), 8.5 (2H, m), 7.2–7.7 (5H, complex), 5.4 (1H, m), 2.9–3.5 (4H, dd), 2.5–2.8 (4H, complex)+3 protons which exchange with D$_2$O.

EXAMPLE 11

N-[2-(4-Isopropoxyphenyl)-1-methylethyl]-2-hydroxy-2-(3-chlorophenyl)ethanamine

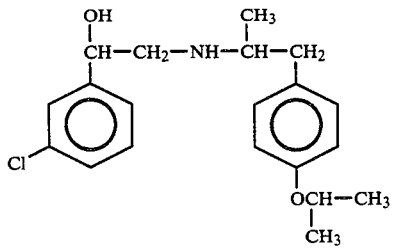

1-(4-Isopropoxyphenyl)propan-2-one (1.92 g) and 2-hydroxy-2-(3-chlorophenyl)ethanamine (1.71 g) were condensed and subsequently reduced with sodium borohydride (2.00 g) by an analogous procedure to that described in Example 1. Chromatography of the crude product on silica gel using 1% methanol-dichloromethane as eluent gave N-[2-(4-isopropoxyphenyl)-1-methylethyl]-2-hydroxy-2-(3-chlorophenyl)ethanamine, mp 58°–61° C. (hexane) as a 42:58 mixture of diastereoisomers.

$^1$Hnmr $\tau$(CDCl$_3$): 8.95 (3H, d), 8.65 (6H, d), 6.95–7.6 (7H, complex; 2H exchange with D$_2$O), 5.25–5.65 (2H, complex), 2.5–3.3 (8H, complex).

EXAMPLE 12

N-[2-(4-$^n$Pentyloxyphenyl)-1-methylethyl]-2-hydroxy-2-(3-chlorophenyl)ethanamine

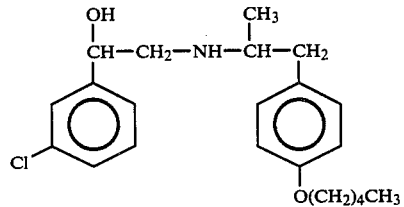

N-[2-(4-$^n$Pentyloxyphenyl)-1-methylethyl]-2-hydroxy-2-(3-chlorophenyl)ethanamine, mp 68°–74° C. (diethyl ether-hexane), was prepared as a 61:39 mixture of diastereoisomers, from 1-(4-$^n$pentyloxyphenyl)propan-2-one (2.22 g) and 2-hydroxy-2-(3-chlorophenyl)ethanamine (1.71 g) by an analogous procedure to that described in Example 1.

$^1$Hnmr $\tau$(CDCl$_3$): 8.8–9.2 (6H, d on m), 8.4–8.7 (4H, m), 8.0–8.3 (2H, m), 6.9–7.7 (7H, m; 2H exchange with D$_2$O), 6.05 (2H, t), 5.4 (1H, m), 2.5–3.25 (8H, complex).

EXAMPLE 13

N-[2-(4-$^n$Decyloxyphenyl)-1-methylethyl]-2-hydroxy-2-(3-chlorophenyl)ethanamine

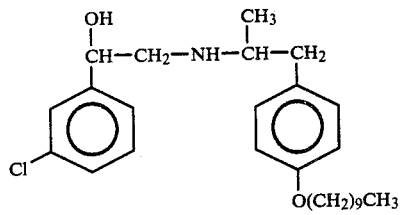

1-(4-$^n$Decyloxyphenyl propan-2-one (2.0 g) and 2-hydroxy-2-(3-chlorophenyl)ethanamine (1.18 g) were condensed and subsequently reduced with sodium borohydride (1.2 g) by an analogous procedure to that described in Example 1. Chromatography of the crude product on silica gel using 1% methanol in dichloromethane as eluent gave N-[2-(4-$^n$decyloxyphenyl)-1-methylethyl]-2-hydroxy-2-(3-chlorophenyl)ethanamine, mp 59°–61° C., as a 44:56 mixture of diastereoisomers.

$^1$Hnmr $\tau$(CDCl$_3$): 8.9–9.25 (6H, d on m), 8.45–8.9 (14H, complex), 8.1–8.4 (2H, m), 6.9–7.7 (7H, complex; 2H exchange with D$_2$O), 6.1 (2H, t), 5.45 (1H, m), 2.55–3.3 (8H, complex).

EXAMPLE 14

N-[2-(4-Methoxyphenyl)ethyl]-2-hydroxy-2-(3-chlorophenyl)ethanamine

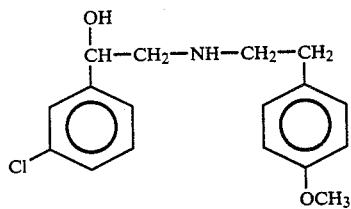

A solution of N-[2-(4-methoxyphenyl)ethyl]-2-hydroxy-1-oxo-2-(3-chlorophenyl)ethanamine (2.8 g) in dry tetrahydrofuran (20 ml) was added slowly to a refluxing suspension of lithium aluminium hydride (1.36 g) in tetrahydrofuran (30 ml) at reflux and then heated under reflux for 24 hours. After careful addition of water (1.4 ml), aqueous sodium hydroxide (10%; 1.4 ml) and water (2.8 ml), filtration and evaporation of the filtrate gave the crude product. Recrystallisation from ethyl acetate-hexane gave N-[2-(4-methoxyphenyl)ethyl]-2-hydroxy-2-(3-chlorophenyl)ethanamine, mp 101°–3° C.

$^1$Hnmr $\tau$(CDCl$_3$): 6.8–7.6 (8H, complex; 2H exchange with D$_2$O), 6.2 (3H, s), 5.35 (1H, q), 2.5–3.3 (8H, complex).

EXAMPLE 15

N-[2-(3-Fluoro-4-methoxyphenyl)-1-methylethyl]-2-hydroxy-2-(3-chlorophenyl)ethanamine-(RS,SR) diastereoisomer

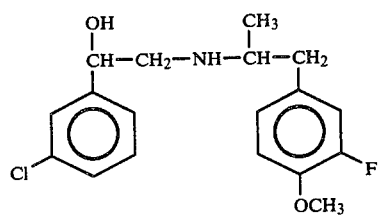

RS, SR diastereoisomer

The mother liquor remaining from the recrystallisation described in Example 4 was concentrated to one-tenth volume, filtered, and the filtrate evaporated to dryness. Aqueous 2M sodium hydroxide solution was added to the residue and the mixture extracted with dichloromethane. The organic extract was dried (magnesium sulphate), filtered and evaporated to dryness to give a crystalline solid. Two recrystallisations from ethyl acetate gave the (RS,SR) diastereoisomer of N-[2-(3-fluoro-4-methoxyphenyl)-1-methylethyl]-2-hydroxy-2-(3-chlorophenyl)ethanamine, mp 106°–7° C. of 90% diastereoisomeric purity.

EXAMPLE 16

N-[3-(4-Methoxyphenyl)-1,1-dimethylpropyl]-2-hydroxy-2-(3-chlorophenyl)ethanamine

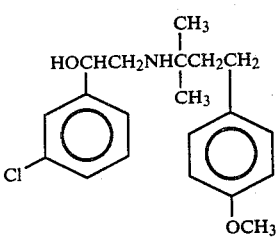

The title compound, was prepared from N-[3-(4-methoxyphenyl)-1,1-dimethylpropyl]-2-hydroxy-1-oxo-2-(3-chlorophenyl)ethanamine by an analogous procedure to that described in Example 14. Chromatography of the crude product on silica gel using 1% methanol in dichloromethane as eluent gave N-[3-(4-Methoxyphenyl)-1,1-dimethylpropyl]-2-hydroxy-2-(3-chlorophenyl)ethanamine, m.p. 50°–53° C. (hexane:diethyl ether).

$^1$H nmr $\tau$(CDCl$_3$): 8.95 (6H,s); 8.6–8.2 (3H,complex m,1H exchanges with D$_2$O); 7.7–7.0 (4H,complex m,); 6.25 (3H,s); 5.46 (1H,q); 3.20 (2H,d); 2.93 (2H,d); 2.8–2.7 (3H,m); 2.63 (1H,s).

EXAMPLE 17

N-[2-(3-Fluoro-4-methoxyphenyl)-1-(R)-1-methylethyl]-2-(R,S)-2-hydroxy-2-(3-chlorophenyl)ethanamine hydrobromide

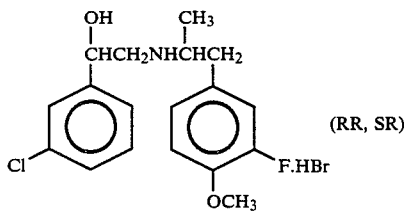
(RR, SR)
.HBr

N-[2-(3-fluoro-4-methoxyphenyl)-1-(R)-1-methylethyl]-2-(R,S)-2-hydroxy-2-(3-chlorophenyl)ethanamine was prepared from N-[2-(3-fluoro-4-methoxyphenyl)-1-(R)-1-methylethyl]-2-(R,S)-2-hydroxy-1-oxo-2-(3-chlorophenyl)ethanamine by an analogous procedure to that described in Example 14. After chromatography over silica, eluting with 1% methanol in dichloromethane the purified amine was dissolved in diethyl ether, cooled and hydrogen bromide passed through the solution. Evaporation of the solvent and recrystallisation of the crude hydrobromide from ethyl acetate:hexane gave N-[2-(3-fluoro-4-methoxyphenyl)-1-(R)-1-methylethyl]-2-(R,S)-2-hydroxy-2-(3-chlorophenyl)ethanamine hydrobromide m.p. 108°–110° C. as a 56:44 mixture of diastereoisomers, $[\alpha]_D^{25} - 12.5°$ (MeOH).

$^1$H nmr $\tau$(d$^6$-DMSO): 8.86 (3H,d); 7.6–6.3 (5H,complex m); 6.18 (3H,s); 5.1–4.8 (1H,m); 3.8–3.5 (1H,m exchanges with D$_2$O); 3.1–2.6 (3H,m); 2.6–2.5 (3H,m); 2.48 (1H,s); 1.7–0.9 (2H,brd m 2H exchanges with D$_2$O).

EXAMPLE 18

N-[2-(4-methoxy-3-methylphenyl)-1-methylethyl]-2-hydroxy-2-(3-chlorophenyl)ethanamine

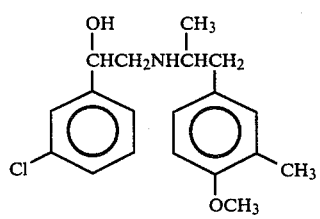

N-[2-(4-methoxy-3-methylphenyl)-1-methylethyl]-2-hydroxy-2-(3-chlorophenyl)ethanamine m.p. 108°–112° C. (hexane:diethyl ether), was prepared as a 32:68 mixture of diastereoisomers from 1-(4-methoxy-3-methylphenyl) propan-2-one (2.72 g) and 2-hydroxy-2-(3-chlorophenyl)ethanamine (2.61 g) by an analogous procedure to that described in Example 1.

- $^1$H nmr $\tau$(CDCl$_3$): 8.97 (3H,d); 7.83 (3H,s); 7.7–6.8 (7H,complex m, 2H exchange with D$_2$O); 6.21 (3H,s); 5.6–5.3 (1H,m); 3.5–3.0 (3H,m); 2.9–2.7 (3H,m); 2.66 (1H,s).

EXAMPLE 19

N-[2-(3,4-Dimethoxyphenyl)-1-methylethyl]-2-hydroxy-2-(3-chlorophenyl)ethanamine

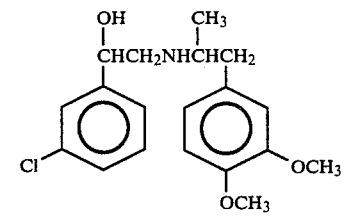

N-[2-(3,4-dimethoxyphenyl)-1-methylethyl]-2-hydroxy-2-(3-chlorophenyl)ethanamine m.p. 79°–83° C. (hexane:diethyl ether), was prepared as a 30:70 mixture of diastereoisomers (after chromatography over silica gel eluting with 1.5% methanol in dichloromethane) from 1-(3,4-dimethoxyphenyl)propan-2-one (1.94 g) and 2-hydroxy-2-(3-chlorophenyl)ethanamine (1.71 g) by an analogous procedure to that described in Example 1.

$^1$H nmr $\tau$(CDCl$_3$): 8.91 (3H,d); 7.9–6.9 (7H,complex m,2H exchange with D$_2$O); 6.13 (6H,s); 5.5–5.2 (1H,m); 3.4–3.0 (3H,m); 2.9–2.4 (4H,m).

EXAMPLE 20

N-[2-(3,4-Dimethoxyphenyl)-1-methylethyl]-2-hydroxy-2-(3-chlorophenyl)ethanamine-(RS,SR) diastereoisomer

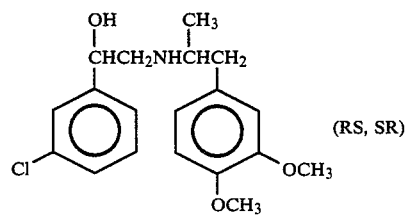
(RS, SR)

N-[2-(3,4-dimethoxyphenyl)-1-methylethyl]-2-hydroxy-2-(3-chlorophenyl)ethanamine-(RS,SR) diastereoisomer, m.p. 94°–97° C. (hexane:diethyl ether), was prepared by fractional recrystallisation of the mixture of diastereoisomers obtained in Example 19.

$^1$H nmr $\tau$(CDCl$_3$): 8.92 (3H,d); 7.6–6.8 (7H,complex m,2H exchange with D$_2$O); 6.12 (6H,s); 5.35 (1H,q); 3.4–3.0 (3H,m); 2.9–2.4 (4H,m).

EXAMPLE 21

N-[2-(4-Cyclohexyloxyphenyl)-1-methylethyl]-2-hydroxy-2-[3-chlorophenyl)ethanamine hydrochloride

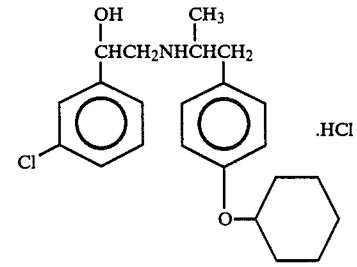
.HCl

N-[2-(4-cyclohexyloxyphenyl)-1-methylethyl]-2-hydroxy-2-(3-chlorophenyl)ethanamine was prepared from 1-(4-cyclohexyloxyphenyl)propan-2-one (2.5 g) and 2-hydroxy-2-(3-chlorophenyl)ethanamine (2.1 g) by an analogous procedure to that described in Example 1. After chromatography on silica gel eluting with 1% methanol in dichloromethane the purified amine was dissolved in diethyl ether, cooled and hydrogen chloride passed through the solution. Evaporation of the solvent and recrystallisation of the crude hydrochloride gave N-[2-(4-cyclohexyloxyphenyl)-1methylethyl]-2-hydroxy-2-(3-chlorophenyl)ethanamine hydrochloride m.p. 164°–166° C. (ethyl acetate-hexane) as a 48:52 mixture of diastereoisomers.

$^1$H nmr $\tau$(d$^6$DMSO): 8.87 (3H,d); 8.8–8.0 (10H complex m); 7.2–6.4 (5H,complex m); 6.0–5.6 (1H,m); 5.1–4.8 (1H,m); 3.65 (1H,d exchanges with D$_2$O); 3.10 (2H,d); 2.84 (2H,d); 2.7–2.5 (4H,m); 1.4–0.9 (1H,brd m exchanges with D$_2$O); 0.7–0.2 (1H,brd m exchanges with D$_2$O).

EXAMPLE 22

N-[2-(4-{2-phenylethoxy}phenyl)-1-methylethyl]-2-hydroxy-2-(3-chlorophenyl)ethanamine

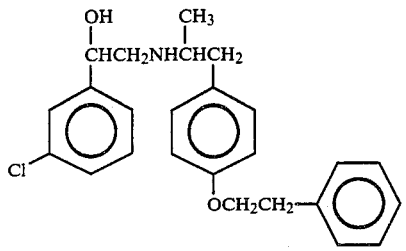

N-[2-(4-{2-phenylethoxy}phenyl)-1-methylethyl]-2-hydroxy-2-(3-chlorophenyl)ethanamine m.p. 112°–114° C. (diethyl ether:ethanol), was prepared as a 5.95 mixture of diastereoisomers from 1-[4-(2-phenylethoxy)-phenyl]propan-2-one (2.0 g) and 2hydroxy-2-(3-chlorophenyl)ethanamine (1.35 g) by an analogous procedure to that described in Example 1.

$^1$H nmr $\tau$(CDCl$_3$): 8.97 (3H,d); 7.8–7.1 (7H,complex m, 2H exchange with D$_2$O); 6.92 (2H,t); 5.83 (2H,t); 5.42 (1H,q); 3.20 (2H,d); 2.96 (2H,d); 2.90–2.50 (9H,complex m).

EXAMPLE 23

N-[2-(3-Methoxyphenyl)-1-methylethyl]-2-hydroxy-2-(3-chlorophenyl)ethanamine hydrochloride

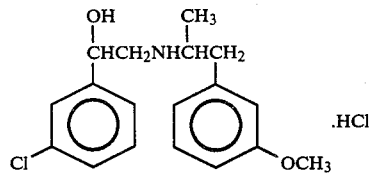

N-[2-(3-methoxyphenyl)-1-methylethyl]-2-hydroxy-2-(3-chlorophenyl)ethanamine was prepared from 1-(3-methoxyphenyl)propan-2-one (3.81 g) and 2-hydroxy-2-(3-chlorophenyl)ethanamine (3.99 g) by an analogous procedure to that described in Example 1 and purified by column chromatography on silica gel using 2–5% methanol in dichloromethane as eluent. The purified amine was converted to its hydrochloride salt by addition of ethereal hydrogen chloride and crystallised from ethyl acetate-diethyl ether to give N-[2-(3-methoxyphenyl)-1-methylethyl]-2-hydroxy-2-(3-chlorophenyl)ethanamine hydrochloride, m.p. 101°–4° C. as u a 60:40 mixture of diastereoisomers.

$^1$H nmr $\tau$(DMSO-d$_6$): 8.85 (3H,d); 7.3 (1H,m); 6.4–7.1 (4H,complex); 6.25 (3H,s); 4.8 (1H,m); 3.6 (1H,s; exchanges with D$_2$O); 3.0–3.3 (3H,complex); 2.4–2.9 (4H,complex); 0.0–1.0 (2H,broad; exchanges with D$_2$O).

EXAMPLE 24

N-[2-(2-Methoxyphenyl)-1-methylethyl]-2-hydroxy-2-(3-chlorophenyl)ethanamine

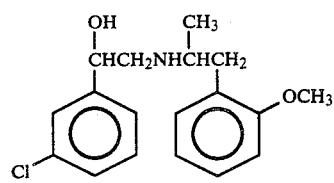

N-[2-(2-methoxyphenyl)-1-methylethyl]-2-hydroxy-2-(3-chlorophenyl)ethanamine, m.p. 85°–7° C. was prepared from 1-(2-methoxyphenyl)propan-2-one (2.69 g) and 2-hydroxy-2-(3-chlorophenyl)ethanamine (2.81 g) as a 32:68 mixture of diastereoisomers, by an analogous procedure to that described in Example 1.

$^1$H nmr $\tau$(CDCl$_3$): 8.95 (3H,d); 6.9–7.65 (7H,complex; 2H exchange with D$_2$O); 6.25 (3H,s); 5.4 (1H,m); 2.45–3.25 (8H,complex).

EXAMPLE 25

N-[2-(3,5-Difluoro-4-methoxyphenyl)-1-methylethyl]-2-hydroxy-2-(3-chlorophenyl)ethanamine hydrochloride

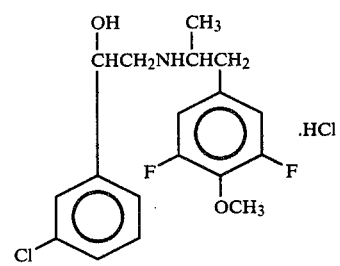

N-[2-(3,5-difluoro-4-methoxyphenyl)-1-methylethyl]-2-hydroxy-2-(3-chlorophenyl)ethanamine hydrochloride, m.p. 120°–140° C. was prepared from 1-(3,5-difluoro-4-methoxyphenyl)propan-2-one (500 mg) and 2-hydroxy-2-(3-chlorophenyl)ethanamine (430 mg) as a 44:56 mixture of diastereoisomers, by an analogous procedure to that described in Example 1.

$^1$H nmr $\tau$(DMSO-d$_6$): 8.9 (3H,d); 6.3–7.4 (5H,complex); 6.2 (3H,s); 4.9 (1H,m); 3.7 (1H,broad, exchange with D$_2$O); 2.4–3.0 (6H,complex); 0.1–1.7 (2H, very broad, exchange with D$_2$O).

DESCRIPTION 1

1-(3-Fluoro-4-methoxyphenyl)-2-nitroprop-1-ene

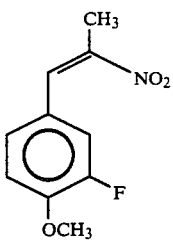

A mixture of 3-fluoro-4-methoxybenzaldehyde (5.0 g) and n-butylamine (5.0 g) in dry benzene (100 ml) was heated under reflux using a Dean and Stark head until the required amount of water had been collected, cooled and solvent removed under vacuum. The residue was dissolved in acetic acid (30 ml), nitroethane (4.0 g) added and the mixture stirred at 100° C. for two hours, cooled, poured into water and filtered to give the title compound.

$^1$Hnmr $\tau$(CDCl$_3$): 7.5 (3H, s), 6.05 (3H, s), 2.6–3.2 (3H, complex), 2.0 (1H, s).

DESCRIPTION 2

1-(3-Fluoro-4-methoxyphenyl)propan-2-one

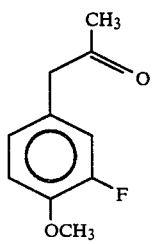

Concentrated hydrochloric acid (30 ml) was added dropwise, over 45 minutes, to a stirred mixture of iron powder (6 g) and 1-(3-fluoro-4-methoxyphenyl)-2-nitroprop-1-ene (5.7 g) in tetrahydrofuran (100 ml) at reflux. The mixture was heated under reflux for a further two hours, cooled, filtered and evaporated. Water (100 ml) was added to the residue and extracted with dichloromethane. The dried (magnesium sulphate) extracts were evaporated to dryness to give the title compound as an oil.

DESCRIPTION 3

4-Isopropoxybenzaldehyde

A mixture of 4-hydroxybenzaldehyde (20 g), anhydrous potassium carbonate (25 g), potassium iodide (0.5 g) and 2-iodopropane (27 g) in 2-butanone (300 ml) was heated overnight, under reflux, with stirring, cooled, filtered and evaporated to dryness. The residue was dissolved in diethyl ether, washed with aqueous sodium hydroxide and brine, dried (magnesium sulphate), filtered and evaporated to dryness. Distillation of the residue gave the title compound, bp 108°–112°/3 mm as an oil.

$^1$Hnmr $\tau$(CDCl$_3$): 8.65 (6H, d), 5.35 (1H, m), 3.1 (2H, d), 2.2 (2H, d), 0.15 (1H, s).

DESCRIPTION 4

1-(4-Isopropoxyphenyl)-2-nitroprop-1-ene

A mixture of 4-isopropoxybenzaldehdye (17.0 g) and n-butylamine (10 g) in toluene was heated under reflux using a Dean and Stark head for two hours, cooled and evaporated to dryness. The residue was dissolved in acetic aid (100 ml), nitroethane (14 ml) added and the mixture heated at 100° C. for 2 hours then poured into water. The crude product was obtained by extracting with diethyl ether, drying (magnesium sulphate), filtering and evaporating the solvent, and used without further purification.

$^1$Hnmr $\tau$(CDCl$_3$): 8.6 (6H, d), 7.55 (3H, s), 5.4 (1H, m), 3.1 (2H, d), 2.6 (2H, d), 2.0 (1H, s).

DESCRIPTION 5

1-(4-Isopropoxyphenyl)propan-2-one

Concentrated hydrochloric acid (90 ml) was added dropwise, over 45 minutes, to a stirred mixture of iron powder (17.5 g) and 1-(4-isopropoxyphenyl)-2-nitroprop1-ene (16.0 g) in tetrahydrofuran (50 ml) at reflux. The mixture was heated under reflux for a further hour, cooled, filtered through diatomaeceous earth and the tetrahydrofuran removed under reduced pressure. The residue was diluted with water, extracted with diethyl ether, washed with brine, dried (magnesium sulphate), filtered and evaporated to dryness. Distillation of the residue gave the title compound, bp 120°–6°/1.5 mm.

$^1$Hnmr $\tau$(CDCl$_3$): 8.7 (6H, d), 7.83 (3H, s), 6.4 (2H, s), 5.5 (1H, m), 2.7–3.3 (4H, dd).

DESCRIPTION 6

4-$^n$Pentyloxybenzaldehyde

The title compound, bp 148°–152°/2 mm, was prepared from 1-bromopentane and 4-hydroxybenzaldehyde by an analogous procedure to that described in Description 3.

$^1$Hnmr $\tau$(CDCl$_3$): 8.0–9.3 (9H, complex), 6.05 (2H, t), 3.05 (2H, d), 2.2 (2H, d), 0.2 (1H, s).

DESCRIPTION 7

1-(4-$^n$Pentyloxyphenyl)-2-nitroprop-1-ene

The title compound was prepared, as an oil, from 4-$^n$pentyloxybenzaldehyde by an analogous procedure to that described in Description 4 and used without further purification.

$^1$Hnmr $\tau$(CDCl$_3$): 8.0–9.3 (9H, complex), 7.5 (3H, s), 5.95 (2H, t), 3.0 (2H, d), 2.5 (2H, d), 1.95 (1H, s).

DESCRIPTION 8

1-(4-$^n$Pentyloxyphenyl)propan-2-one

The title compound, bp 140°–150°/1.5 mm, was prepared from 1-(4-$^n$pentyloxyphenyl)-2-nitroprop-1-ene, by an analogous procedure to that described in Description 5.

$^1$Hnmr $\tau$(CDCl$_3$): 8.05–9.3 (9H, complex), 7.9 (3H, s), 6.4 (2H, s), 6.1 (2H, t), 2.7–3.3 (4H, dd).

DESCRIPTION 9

4-$^n$Decyloxybenzaldehyde

4-Hydroxybenzaldehyde (12.2 g) was added to a solution of sodium ethoxide (prepared by addition of sodium (2.5 g) to ethanol (100 ml)) in ethanol and stirred for 15 minutes. $^n$Decylbromide (22.0 g) in ethanol (50 ml) was added and the mixture heated under reflux for one day, cooled, filtered and evaporated to dryness. The residue was dissolved in diethyl ether, washed with aqueous sodium hydroxide, dried (magnesium sulphate), filtered and evaporated to dryness. Distillation of the residue gave the title compound, bp 206°–8°/4 mm.

$^1$Hnmr $\tau$(CDCl$_3$): 7.95–9.4 (19H, complex), 6.0 (2H, t), 3.0 (2H, d), 2.20 (2H, d), 0.1 (1H, s).

DESCRIPTION 10

1-(4-$^n$Decyloxyphenyl)-2-nitroprop-1-ene

The title compound was prepared, as a solid, from 4-$^n$decyloxybenzaldehyde by an analogous procedure to that described in Description 4, and subsequently used without further purification.

$^1$Hnmr $\tau$(CDCl$_3$): 8.0–9.3 (19H, complex), 7.5 (3H, s), 6.0 (2H, t), 3.05 (2H, d), 2.55 (2H, d), 1.95 (1H, s).

DESCRIPTION 11

1-(4-$^n$Decyloxyphenyl)propan-2-one

The title compound, bp 190°–5°/1 mm, was prepared from 1-(4-$^n$decyloxyphenyl)-2-nitroprop-1-ene by an analogous procedure to that described in Description 5.

$^1$Hnmr $\tau$(CDCl$_3$): 8.0–9.3 (19H, complex), 7.85 (3H, s), 6.4 (2H, s), 6.05 (2H, t), 2.8–3.4 (4H, dd).

DESCRIPTION 12

N-[2-(4-Methoxyphenyl)ethyl]-2-hydroxy-1-oxo-2-(3-chlorophenyl)ethanamine

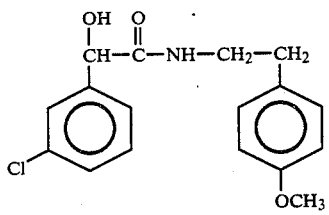

Dicyclohexylcarbodiimide (2.00 g) in N,N-dimethylformamide (10 ml) was added to a solution of 1-hydroxybenzotriazole (1.37 g), 2-(4-methoxyphenyl)ethanamine (1.51 g) and 3-chloromandelic acid (1.86 g) in N,N-dimethylformamide (40 ml) and the mixture stirred for 18 hours, filtered then evaporated to dryness. The residue was dissolved in dichloromethane, washed with aqueous 4M hydrochloric acid and sodium bicarbonate solution, dried (magnesium sulphate), filtered and evaporated to dryness to give the title compound as an oil which was used without further purification.

$^1$Hnmr $\tau$(CDCl$_3$): 7.3 (2H, t), 6.55 (2H, m), 6.25 (3H, s), 5.05 (1H, s), 2.9–3.3 (4H, complex), 2.55–2.85 (4H, complex).

DESCRIPTION 13

N-[3-(4-Methoxyphenyl)-1,1-dimethylpropyl]-2-hydroxy-1-oxo-2-(3-chlorophenyl)ethanamine

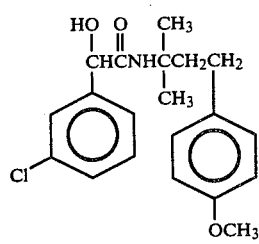

The title compound was prepared from 3-chloromandelic acid (2.1 g) and 3-(4-methoxyphenyl)-1,1-dimethylpropanamine (1.9 g) by an analogous procedure to that described in Description 12 and used without further purification.

$^1$H nmr $\tau$(CDCl$_3$): 8.67 (6H,s); 8.5–7.5 (4H,m); 6.26 (3H,s); 5.07 (1H,s); 3.9–3.7 (1H,m); 3.30 (2H,d); 3.03 (2H,d); 2.8–2.0 (4H,m).

DESCRIPTION 14

N-[2-(3-Fluoro-4-methoxyphenyl)-1-(R)-1-methylethyl]-2-(R,S)-2-hydroxy-1-oxo-2-(3-chlorophenyl)ethanamine

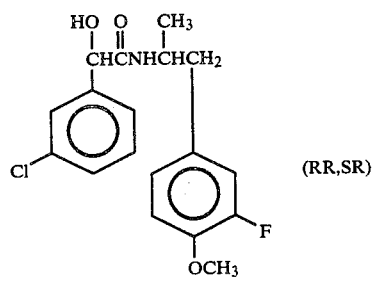

(RR,SR)

The title compound was prepared from 3-chloromandelic acid (2.2 g) and (R)-2-amino-1-(3-fluoro-4-methoxyphenyl)propane by an analogous procedure to that described in Description 12 and used without further purification.

DESCRIPTION 15

1-(4-Methoxy-3-methylphenyl)-2-nitroprop-1-ene

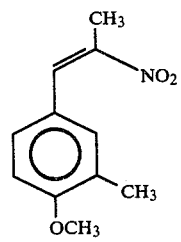

The title compound was prepared from 4-methoxy-3-methylbenzaldehyde by an analogous procedure to that described in Description 1 and used without further purification.

DESCRIPTION 16

1-(4-Methoxy-3-methylphenyl)propan-2-one

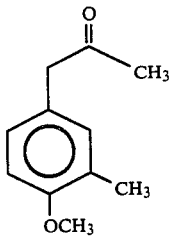

Acetic acid (210 ml) was added dropwise, over a period of 30 minutes to a stirred mixture of iron powder (56 g), 1-(4-methoxy-3-methylphenyl)-2-nitroprop-1-ene (18.0 g) and water (20 ml) in methanol (150 ml) under reflux.

After 3 hours the reaction mixture was cooled and added to a mixture of water (500 ml) and dichloromethane (200 ml) and filtered through diatomacous earth. Separation of the organic phase, drying and evaporation furnished the crude ketone. Distillation, afforded the title compound bp 115°–120°/1.5 mmHg as an oil.

$^1$H nmr $\tau$(CDCl$_3$): 7.88 (3H,s); 7.78 (3H,s); 6.40 (2H,s); 6.22 (3H,s); 3.4–2.8 (3H,m).

DESCRIPTION 17

2-Methyl-2-(4-hydroxyphenyl)methyl-1,3-dioxalane

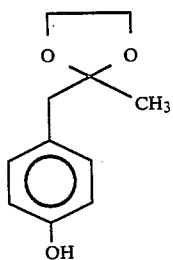

To a mixture of sodium iodide (51 g) and 1-(4-benzyloxyphenyl)propan-2-one (53 g) in acetonitrile (250 ml) at 50° was added chlorotrimethylsilane (43 ml) with vigorous stirring. After 2 hours the reaction was cooled and quenched with methanol (25 ml). The solvent was evaporated and the residue dissolved in diethyl ether, the organic phase was washed with saturated sodium thiosulphate solution. Extraction of the resultant ethereal solution with sodium hydroxide solution (10% w/v), acidification of the aqueous phase, extraction with dichloromethane, drying and evaporation of the organic extract afforded 1-(4-hydroxyphenyl)-propan-2-one as an oil. Conversion to the dioxalane was achieved by boiling a mixture of 1-(4-hydroxy-phenyl)-propan-2-one (25 g), 1,2-dihydroxyethane (10 ml) 4-toluenesulphonic acid (0.5 g) and toluene (250 ml) in conjunction with a water separator. After 18 hours, the mixture was cooled, washed with water, dried and evaporated to dryness to give the title compound as an oil.

$^1$H nmr $\tau$(CDCl$_3$): 8.68 (3H,s); 7.13 (2H,s); 6.4–6.0 (4H,m); 3.30 (2H,d); 2.88 (2H,d).

DESCRIPTION 18

1-(4-Cyclohexyloxyphenyl)propan 2-one

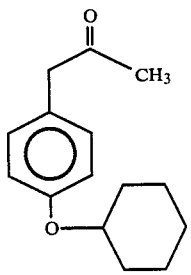

To a mixture of sodium hydride (a 1:1 dispersion in oil), previously washed with dry hexane, and dry dimethylformamide (5 ml) was added 2-methyl-2-(4-hydroxyphenyl)methyl-1,3-dioxalane (3.68 g) in dry dimethylformamide (50 ml). The reaction mixture was stirred under an atmosphere of nitrogen for 0.25h. Cyclohexyl 4-toluenesulphonate (5.0 g) in dry dimethylformamide (50 ml) was added and the resultant mixture stirred at 140° C. for 2 hours. The reaction was cooled and quenched with water (250 ml), extraction of the aqueous phase with diethyl ether, separation, drying and evaporation of the organic phase gave an oil which was treated with 2M hydrochloric acid in methanol for 18 hours at room temperature. Evaporation, addition of water and extraction of the aqueous solution with dichloromethane, followed by drying and evaporation of the organic phase gave the title compound as an oil.

DESCRIPTION 19

1-[4-(2-phenylethoxy)phenyl]propan-2-one

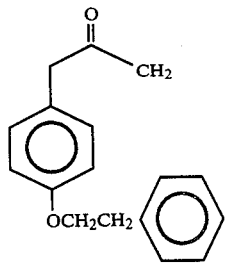

To a mixture of 2-methyl-2-(4-hydroxyphenyl) methyl-1,3-dioxalane (6.4 g), triphenylphosphine (9.g) and 2-phenylethanol in diethyl ether (150 ml) at 0°, under an atmosphere of nitrogen, with stirring was added dropwise (maintaining the reaction temperature below 20°) diethylazodicarboxylate (5.5 g) in diethyl ether (10 ml). After 0.5 hours at 0° the reaction was stirred at room temperature for 18 hours. The resultant solution was filtered, washed with 10% hydrochloric acid and saturated sodium carbonate solution, and evaporated to give the crude ketone. Chromatography over silica eluting with hexane:acetone gave the title compound as an oil.

$^1$H nmr $\tau$(CDCl$_3$): 7.98 (3H,s); 7.00 (2H,t); 6.48 (2H,s); 5.92 (2H,t); 3.20 (2H,d); 2.95 (2H,d); 2.8–2.5 (5H,m).

DESCRIPTION 20

1-(3,5 Difluoro-4-methoxyphenyl)propan-2-one (i) 2-Chloro-1-(3,5-difluoro-4-methoxyphenyl)propan-1-one

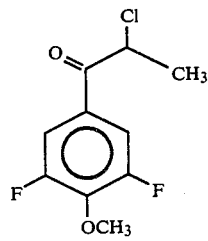

2-Chloropropionylchloride (5.7 g) was added, dropwise, under nitrogen gas, to a stirred slurry of aluminium chloride (6.0 g) in 1,2-dichloroethane (75 ml). The mixture was stirred at ambient temperature for 15 minutes. 3,5-Difluoroanisole (6.5 g) was added dropwise to the stirred mixture. The reaction mixture was then stirred at ambient temperature for 16 hours and poured onto an ice-water mixture. The organic layer was separated and the aqueous layer was extracted with 1,2-dichloroethane. The combined organic layers were washed with water, dried (magnesium sulphate) and concentrated to give 2-chloro-1-(3,5-difluoro-4-methoxyphenyl)propan-1-one as an oil which was used in the next stage without further purification.

(ii) 1-(3,5-Difluoro-4-methoxyphenyl)propan-1,2-diol

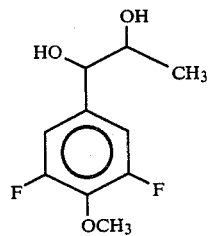

Potassium acetate (3.0 g) then glacial acetic acid (5 ml) and then sodium iodide (1.0 g) were added to a solution of 2-chloro-1-(3,5-difluoro-4-methoxyphenyl)propan-1-one (6.5 g) in acetone (50 ml). The mixture was stirred and heated under reflux for 4 hours, cooled and treated with water (150 ml) the acetone was evaporated and the aqueous residue was extracted into dichloromethane. The organic phase was washed with sodium bicarbonate solution, dried (magnesium sulphate), and concentrated under reduced pressure, the residual oil was dissolved in ethanol (150 ml) cooled in ice and treated with excess sodium borohydride (1.5 g). The solution was stirred for 2 hours at ambient temperature, the ethanol and the residue partitioned between dilute hydrochloric acid and ethyl acetate. The ethyl acetate layer was dried (magnesium sulphate) and evaporated to give 1-(3,5-difluoro-4-methoxy-phenyl)propane 1,2-diol as an oil which was used in the next stage without further purification.

(iii) 1-(3,5-Difluoro-4-methoxyphenyl)propan-2-one

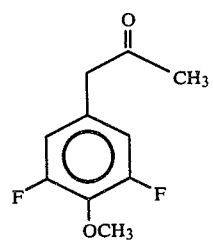

A mixture of 1-(3,5-Difluoro-4-methoxyphenyl)-propane-1,2-diol (4.5 g) and p-toluenesulphonic acid (0.15 g) in benzene (100 ml) was heated under reflux with azeotropic removal of water using a Dean and Stark head for 2 hours. The solvent was removed by evaporation under reduced pressure and the residue partitioned between water and dichloromethane. The organic layer was washed with water, and sodium bicarbonate solution, dried (magnesium sulphate) and concentrated to give an oil which was purified by column chromatography on silica gel to give 1-(3,5-difluror-4-methoxyphenyl)propan-2-one as a gum.

$^1$H nmr $\tau$(CDCl$_3$): 7.8 (3H,s); 6.4 (2H,s); 6.0 (3H,s); 2.8–3.4 (2H,m).

Demonstration of Effectiveness of Compounds (i) Anti-hyperglycaemic activity

Female CFLP mice, each weighing approximately 25 g were fasted for 24 hours prior to the study. The compounds under study were administered orally as an aqueous solution to each of 6 mice. 6 mice were given water as a control. 30 minutes later a blood sample (20 μl) was obtained from the tail for the analysis of blood glucose. Immediately after taking this blood sample, glucose (1 g/kg body weight) was administered subcutaneously to each mouse. Blood samples were then obtained from each mouse at 30 minute intervals for 120 minutes.

Compounds that produced a significant ($P<0.05$) reduction of blood glucose, compared with control mice given water, at any time interval, were considered active. The area under the blood glucose curve over the 2 hour period after the adminstration of the glucose was calculated for each compound and compared with the value for control animals.

| Compound of Example No | Dose (μmoles/kg po) | Reduction in area under blood glucose curve (%) |
|---|---|---|
| Control | — | 0 |
| 1 | 1 | 36 |
| 2 | 1 | 47 |
| 3 | 1 | 46 |
| 4 | 1 | 42 |
| 5 | 1 | 49 |
| 6 | 0.5, 1 | 30, 40 |
| 7 | 5.0 | 32 |
| 8 | 1 | 30 |
| 9 | 1 | 40 |
| 10 | 1 | 47 |
| 11 | 0.2 | 12.5 |
| 12 | 0.5 | 36 |
| 13 | 1 | 22 |
| 14 | 1 | 39 |
| 15 | 1 | 19 |
| 16 | 50 | 21 |
| 17 | 2.5 | 38 |

-continued

| Compound of Example No | Dose (μmoles/kg po) | Reduction in area under blood glucose curve (%) |
|---|---|---|
| 18 | 2.5 | 58 |
| 19 | 2.5 | 21 |
| 20 | 2.5 | 34 |
| 21 | 2.5 | 53 |
| 22 | 2.5 | 13 |
| 23 | 2.5 | 22 |
| 24 | 5.0 | 27 |

Toxicity

No toxicity was observed during the above experiments.

(ii) Effect on energy expenditure

The effect of the compounds on the energy expenditure of mice was demonstrated by means of the following procedure.

Female CFLP mice each weighing approximately 24 g, were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content following the principles described by J. B. de V Weir, J. Physiol (London), 109, 1–9 (1949). The food intake of the mice was measured over this same period of 21 hours. The results are expressed as a percentage of the mean food intake or rate of energy expenditure of the mice dosed with water.

| Compound of Example No | Dose (mg/kg po) | Mean Energy Expenditure (%) 0–3 h | Mean Energy Expenditure (%) 0–21 h | Mean Food Intake (%) |
|---|---|---|---|---|
| Control | — | 100 | 100 | 100 |
| 1 | 26.1 | — | 129 | 98 |
| 2 | 17.0 | — | 120 | 97 |
| 3 | 19.0 | — | 115 | 77 |
| 4 | 23.3 | 145 | 115 | 81 |
| 5 | 8.9 | 133 | 108 | 78 |
| 7 | 16.9 | 141 | 108 | 89 |
| 8 | 20.3 | 161 | 138 | 94 |
| 9 | 18.8 | 151 | 127 | 89 |
| 10 | 17.0 | 156 | 120 | 97 |
| 11 | 19.3 | 165 | 122 | 59 |
| 12 | 20.9 | 146 | 128 | 85 |
| 13 | 24.8 | 139 | 117 | 89 |
| 14 | 17.0 | 150 | 116 | 80 |
| 16 | 19.3 | 110 | 96 | 81 |
| 17 | 20.9 | 150 | 114 | 87 |
| 18 | 18.6 | 141 | 115 | 94 |
| 19 | 17.5 | 169 | 125 | 71 |
| 20 | 19.4 | 168 | 130 | 108 |
| 21 | 23.6 | 134 | 109 | 83 |
| 22 | 20.5 | 127 | 107 | 88 |
| 23 | 19.8 | 142 | 116 | 103 |
| 25 | 19.5 | 150 | 119 | 95 |

(iii) Cardiac Activity

Rat hearts were perfused by the Langendorff procedure as follows:

Hearts were dissected free within 30 seconds of death and reverse perfused via the aorta and coronary vessels with Krebs-Ringer bicarbonate solution (pH 7.4, 37° C.) gassed with 95% oxygen:5% carbon dioxide at a flow rate between 8–12 cm$^3$/minute. Responses were observed after injection of drug dissolved in isotonic saline into the perfusion media. Heart rate and tension were displayed on an Ormed MX2P recorder via a tension transducer and heart ratemeter.

Results are expressed as a percentage of the maximum response due to salbutamol.

| Compound of Example No | Dose added to perfusate (μg) | Heart Tension | Heart Rate |
|---|---|---|---|
| Salbutamol | — | 100 | 100 |
| 1 | 10 | 7 | 0 |
| 2 | 10 | 26 | 14 |
| 3 | 10 | 36 | 0 |

(iv) Platelet aggregation inhibition activity

Male CFLP mice (ca 20 g, n=8) were dosed orally with compound or vehicle (controls) after an overnight fast. Two hours later each mouse received an intravenous dose of collagen (400 μg/kg, pH 6–6.6). Exactly 30 seconds after injection of collagen, each mouse was placed in a chamber of $CO_2$ until respiration ceased. Blood platelet count was determined (Ultra-Flo 100 whole blood platelet counter, Clay Adams) in blood samples (3 μl) taken immediately from the inferior vena cava. Each blood platelet count was expressed as a percent of that obtained in a tail blood sample taken immediately before injection of collagen. Results are given in the table below.

| COMPOUND OF EXAMPLE NO | DOSE po μmol/kg | % INHIBITION OF RESPONSE TO COLLAGEN |
|---|---|---|
| Aspirin | 600 | 33 |
| 2 | 5 | 40 |
| 10 | 5 | 40 |

(v) Anti-inflammatory Activity

The method used is based on that described by G. Tonelli et al (Endocrinology, 77, 625–634, 1965). An inflammation is induced in the rat ear by the application of 50 μl of a 1% solution of croton oil in tetrahydrofuran, test compounds being dissolved in the irritant vehicle. After 6 hours the inflammation is assessed by killing the animals and weighing the ears. Topical anti-inflammatory activity of a compound is generally considered to be shown when a significant (5% level) reduction in ear weight is seem compared to non-drug treated control.

| COMPOUND OF EXAMPLE NO | DOSE mg/rat ear | ACTIVITY |
|---|---|---|
| 5 | 1.0 | Active |

We claim:

1. A compound of formula (II):

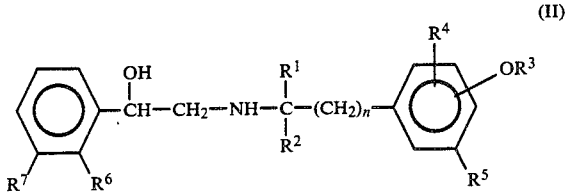

or salt thereof; wherein
R$^1$ is hydrogen or methyl,
R$^2$ is hydrogen or methyl,
R$^3$ is hydrogen, C$_{1-12}$ straight or branched alkyl, C$_{3-10}$ cycloalkyl, phenyl(C$_{1-4}$)-alkyl or benzyl optionally substituted by C$_{1-4}$ alkyl, C$_{1-4}$ alkoxy or halogen;
R$^4$ is hydrogen, halogen, hydroxy, C$_{1-4}$ alkyl or C$_{1-4}$ alkoxy,
R$^5$ is hydrogen or fluorine,
R$^6$ is hydrogen or fluorine,
R$^7$ is halogen; and
n is 1 or 2,
provided that when R$^1$, R$^2$, R$^5$ and R$^6$ are each hydrogen, −OR$^3$ is p-methoxy, R$^4$ is methoxy, R$^7$ is chloro and n is 1, then R$^4$ is ortho to the group —(CH$_2$)$_n$—.

2. A compound as claimed in claim 1 wherein n is 1.
3. A compound as claimed in claim 1 wherein R$^1$ is hydrogen and R$^2$ is methyl.
4. A compound as claimed in claim 2 wherein R$^4$ is hydrogen or fluorine.
5. A compound as claimed in claim 3 wherein R$^7$ is chlorine.
6. A compound as claimed in claim 1 and selected from:
N-[2-(4-Benzyloxyphenyl)-1-methylethyl]-2-hydroxy-2-(3-chlorophenyl)ethanamine;
N-[2-(4-Hydroxyphenyl)-1-methylethyl]-2-hydroxy-2-(3-chlorophenyl)ethanamine;
N-[2-(3-Fluoro-4-methoxyphenyl)-1-methylethyl]-2-hydroxy-2-(3-chlorophenyl)ethanamine;
N-[2-(3-Fluoro-4-methoxyphenyl)-1-methylethyl]-2-hydroxy-2-(3-chlorophenyl)ethanamine-as the racemic pair of RS and SR enantiomers;
N-[2-(4-Methoxyphenyl)-1-methylethyl]-2-hydroxy-2-(3-chlorophenyl)ethanamine;
N-[2-(4-Methoxyphenyl)-1-methylethyl]-2-hydroxy-2-(3-chlorophenyl)ethanamine-as the racemic pair of RS and SR enantiomers;
N-[2-(4-Methoxyphenyl)-1-methylethyl]-2-hydroxy-2-(3-fluorophenyl)ethanamine;
N-[2-(4-Methoxyphenyl)-1-methylethyl]-2-hydroxy-2-(3-bromophenyl)ethanamine;
N-[2-(4-Methoxyphenyl)-1-methylethyl]-2-hydroxy-2-(3-chloro-2-fluorophenyl)ethanamine;
N-[3-(4-Hydroxyphenyl)-1-methylpropyl]-2-hydroxy-2-(3-chlorophenyl)ethanamine;
N-[2-(4-Isopropoxyphenyl)-1-methylethyl]-2-hydroxy-2-(3-chlorophenyl)ethanamine;
N-[2-(4-nPentyloxyphenyl)-1-methylethyl]-2-hydroxy-2-(3-chlorophenyl)ethanamine;
N-[2-(4-nDecyloxyphenyl)-1-methylethyl]-2-hydroxy-2-(3-chlorophenyl)ethanamine;
N-[2-(4-Methoxyphenyl)ethyl]-2-hydroxy-2-(3-chlorophenyl)ethanamine;
N-[2-(3-Fluoro-4-methoxyphenyl)-1-methylethyl]-2-hydroxy-2-(3-chlorophenyl)ethanamine-as the racemic pair of RS and SR enantiomers;
N-[3-(4-Methoxyphenyl)-1,1-dimethylpropyl]-2-hydroxy-2-(3-chlorophenyl)ethanamine;
N-[2-(3-Fluoro-4-methoxyphenyl)-1-(R)-1-methylethyl]-2-(R,S)-2-hydroxy-2-(3-chlorophenyl)ethanamine;
N-[2-(4-Methoxy-3-methylphenyl)-1-methylethyl]-2-hydroxy-2-(3-chlorophenyl)ethanamine;
N-[2-(3,4-Dimethoxyphenyl)-1-methylethyl]-2-hydroxy-2-(3-chlorophenyl)ethanamine;
N-[2-(3,4-Dimethoxyphenyl)-1-methylethyl]-2-hydroxy-2-(3-chlorophenyl)ethanamine-as the racemic pair of RS and SR enantiomers;
N-[2-(4-Cyclohexyloxyphenyl)-1-methylethyl]-2-hydroxy-2-(3-chlorophenyl)ethanamine;
N-[2-(4- (2-phenylethoxy) phenyl)-1-methylethyl]-2-hydroxy-2-(3-chlorophenyl)ethanamine;
N-[2-(3-Methoxyphenyl)-1-methylethyl]-2-hydroxy-2-(3-chlorophenyl)ethanamine;
N-[2-(2-Methoxyphenyl)-1-methylethyl]-2-hydroxy-2-(3-chlorophenyl)ethanamine;
N-[2-(3,5-Difluoro-4-methoxyphenyl)-1-methyl-ethyl]-2-hydroxy-2-(3-chlorophenyl)ethanamine;
and salts thereof, 7. A pharmaceutical composition comprising a compound of formula (X):

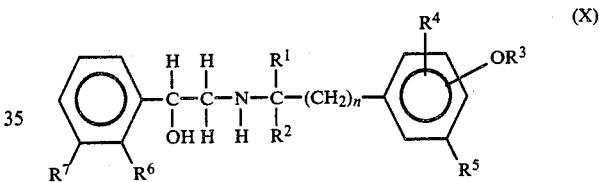

or a salt thereof; wherein
R$^1$ is hydrogen or methyl,
R$^2$ is hydrogen or methyl,
R$^3$ is hydrogen, C$_{1-2}$ straight or branched alkyl C$_{3-10}$ cycloakyl or phenyl (C$_{1-4}$) alkyl or benzyl optionally substituted by C$_{1-4}$ alkyl, C$_{1-4}$ alkoxy or halogen;
R$^4$ is hydrogen, halogen, hydroxy, C$_{1-4}$ alkyl or C$_{1-4}$ alkoxy,
R$^5$ is hydrogen or fluorine,
R$^6$ is hydrogen or fluorine,
R$^7$ is halogen, and
n is 1 or 2,
in association with a pharmaceutically acceptable carrier.

8. A composition as claimed in claim 7 presented in unit dosage form.
9. The compound according to claim 1, wherein n is 1, R$^1$ is hydrogen, R$^2$ is methyl, R$^4$ is hydrogen or fluorine, and R$^7$ is chlorine.
10. The compound according to claim 7, wherein n is 1, R$^1$ is hydrogen, R$^2$ is methyl, R$^4$ is hydrogen or fluorine, and R$^7$ is chlorine.
11. The composition according to claim 7, containing 0.1 to 500 mg of said compound.
12. A compound of the formula

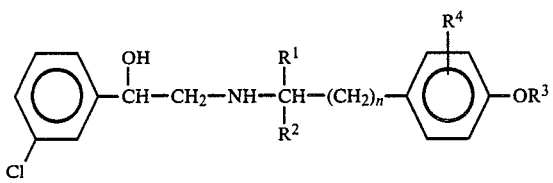

or salt thereof; wherein $R^1$ is hydrogen or methyl;

$R^2$ is hydrogen or methyl;

$R^3$ is hydrogen, $C_{1-12}$ straight or branched alkyl, $C_{3-10}$ cycloakyl, phenyl($C_{1-4}$)- alkyl or benzyl optionally substituted by $C_{1-4}$ alkyl, $C_{1-4}$ alkoxy or halogen;

$R^4$ is hydrogen, halogen, hydroxy, $C_{1-4}$ alkyl or $C_{1-4}$ alkoxy; and n is 1 or 2.

13. A compound as claimed in claim 12, wherein $R^1$ is hydrogen and $R^2$ is methyl.

14. A compound as claimed in claim 13, wherein $R^4$ is hydrogen or fluorine.

15. A compound according to claim 14, wherein $R^3$ is methyl.

16. A compound of the formula

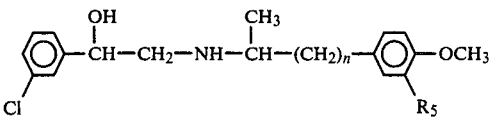

or salt thereof; wherein $R^5$ is hydrogen or fluorine and n is 1 or 2.

17. A compound as claimed in claim 16, which is N-[2-(3-fluoro-4-methoxyphenyl)-1-methylethyl]-2-hydroxy-2-(3-chlorophenyl)ethanamine.

18. A compound as claimed in claim 17, which is N-[2-(4-methoxyphenyl)-1-methylethyl]-2-hydroxy-2-(3-chlorophenyl) ethanamine.

19. A compound as claimed in claim 17, which is N-[2-(4-methoxyphenyl)-1-methlethyl]-2-hydroxy,-2-(3-chlorophenyl)ethanamine hydrobromide-as the racemic pair of RR and SS enantiomers.

20. A compound as claimed in claim 1 wherein the carbon atom bearing the hydroxy and the m-halophenyl group,

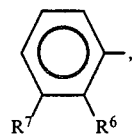

has the R-configuration.

21. A compound as claimed in claim 1, wherein when $R^1$ and $R^2$ are different, both asymmetric carbon atoms are in the R-configuration.

* * * * *